(12) United States Patent
Pelizzone et al.

(10) Patent No.: US 9,511,226 B2
(45) Date of Patent: Dec. 6, 2016

(54) DEVICE AND METHOD FOR ELECTRICAL STIMULATION OF NEURAL OR MUSCULAR TISSUE

(71) Applicants: Les Hôpitaux Universitaires de Genève, Genève (CH); Université de Genève, Genève (CH)

(72) Inventors: Marco Pelizzone, Genève (CH); Angélica Perez Fornos, Bernex (CH); Maurizio Ranieri, Genève (CH); Samuel Cavuscens, Tannay (CH)

(73) Assignees: LES HOPITAUX UNIVERSITAIRES DE GENÈVE, Genève (CH); Université de Genéve, Genève (CH)

( * ) Notice: Subject to any disclaimer, the term of this patent is extended or adjusted under 35 U.S.C. 154(b) by 0 days.

(21) Appl. No.: 14/764,965

(22) PCT Filed: Jan. 24, 2014

(86) PCT No.: PCT/EP2014/051450
§ 371 (c)(1),
(2) Date: Jul. 30, 2015

(87) PCT Pub. No.: WO2014/118094
PCT Pub. Date: Aug. 7, 2014

(65) Prior Publication Data
US 2016/0001075 A1  Jan. 7, 2016

(30) Foreign Application Priority Data

Jan. 30, 2013  (EP) .................................... 13153300

(51) Int. Cl.
*A61N 1/00* (2006.01)
*A61N 1/36* (2006.01)
*A61N 1/05* (2006.01)

(52) U.S. Cl.
CPC ......... *A61N 1/36032* (2013.01); *A61N 1/0541* (2013.01)

(58) Field of Classification Search
CPC combination set(s) only.
See application file for complete search history.

(56) References Cited

U.S. PATENT DOCUMENTS 6,636,768 B1  10/2003  Harrison
7,647,120 B2  1/2010  Della Santina et al.
(Continued)

FOREIGN PATENT DOCUMENTS

WO  WO 2010/135783 A1  12/2010
WO  WO 2012/012634 A1  1/2012
WO  WO 2013/134873 A1  9/2013

OTHER PUBLICATIONS

Guyot, Jean-Philippe, et al., "Eye Movements in Response to Electric Stimulation of the Lateral and Superior Ampullary Nerves," *Annals of Otology, Rhinology, and Laryngology*, vol. 120, No. 2, pp. 81-87 (2011).
(Continued)

*Primary Examiner* — Robert N Wieland
(74) *Attorney, Agent, or Firm* — Christensen Fonder P.A.

(57) ABSTRACT

A device for electrical stimulation of neural and/or muscular tissue. The device includes a cochlear implant being equipped with a power source, a speech processor, a microphone adapted to deliver sound signals to said speech processor, a current stimulator, at least an array of electrodes attached to the stimulator, and at least a signal sensor other than the microphone. The device further includes a signal transformation unit, said signal sensors being adapted to capture relevant input information and to deliver a corresponding input signal to the transformation unit, the latter allowing to transform said input signal received from the signal sensors into a modulated electrical output signal adapted to be treated by the speech processor of the cochlear implant.

27 Claims, 2 Drawing Sheets

(56) References Cited

U.S. PATENT DOCUMENTS

| | | | |
|---|---|---|---|
| 2010/0010570 A1* | 1/2010 | Grayden | A61N 1/36032 607/57 |
| 2011/0249835 A1* | 10/2011 | Lunner | H04R 25/505 381/312 |
| 2012/0197345 A1 | 8/2012 | Staller | |
| 2015/0032186 A1* | 1/2015 | Cushing | A61N 1/36032 607/57 |

OTHER PUBLICATIONS

Guyot, Jean-Philippe, et al., "Adaptation to steady-state electrical stimulation of the vestibular system in the human," *Annals of Otology, Rhinology, and Laryngology*, vol. 120, No. 3, pp. 143-149 (2011).

Pelizzone, Marco, et al., "Vestibular implants: First experiments in Humans," *Hôpitaux Universitaires de Genève*, 34 pgs.

* cited by examiner

DEVICE AND METHOD FOR ELECTRICAL STIMULATION OF NEURAL OR MUSCULAR TISSUE

PRIORITY CLAIM

The present application is a National Phase entry of PCT Application No. PCT/EP2014/051450, filed Jan. 24, 2014, which claims priority from European Patent Application Number 13153300.2, filed Jan. 30, 2013, the disclosures of which are hereby incorporated by reference herein in their entirety.

FIELD OF THE INVENTION

The present invention pertains to a device, respectively a method for electrical stimulation of neural and/or muscular tissue, such a device comprising a cochlear implant being equipped with a power source, a speech processor, a microphone adapted to deliver sound signals to said speech processor, a current stimulator, at least an array of electrodes attached to the stimulator, and at least a signal sensor other than said microphone.

BACKGROUND OF THE INVENTION

In general, the present invention is situated in the context of neuroprostheses, and in particular is closely related to cochlear implants adapted for treatment of hearing loss in situations where conventional hearing aids cannot be used to sufficiently restore the auditory function of the patient but where the patient's auditory nerve is still operational. Specifically, cochlear implants are very advanced medical devices that transform speech, i.e., sound waves, into electrical current signals which are delivered, by bypassing malfunctioning or damaged structures of the ear, directly to the auditory nerve of deaf patients. Stimulated in such way, the auditory nerve then sends these artificial signals to the brain which recognizes them as sound, allowing the restoration of some auditory perception. The results are quite impressive, allowing for example post-lingually deafened, implanted adults to make use again of telephones or pre-lingually deafened, sufficiently early implanted children to develop oral language as their principal means of communication and attend normal schools with their hearing peers.

Cochlear implants now have a successful clinical history of more than 25 years with more than 300,000 implanted patients worldwide. Therefore, these devices nowadays can be considered to be very reliable, whilst for other medical applications requiring implantable functional electrical stimulators of neural or muscular tissue corresponding devices with similar reliability and well proven functionality currently do not exist.

Nevertheless, there have been efforts to realize similar devices for use as neuroprostheses in other medical applications like the restoration of the vestibular function of patients with balance disorders. Such systems need to capture the motion of the head of the patient via motion sensors like gyroscopes and/or accelerometers and to output a pattern of electrical impulses adapted to stimulate the different branches of the vestibular nerve.

Examples of such approaches are disclosed, amongst others, in documents WO2012/012634 describing a vestibular implant system with internal and external motion sensors, U.S. Pat. No. 7,647,120 describing a dual cochlear/vestibular stimulator, and WO2010/135783 describing a vestibular stimulation array of electrodes specifically adapted for implantation in a semicircular canal of the vestibular system, all of which are incorporated herein by reference in their entireties. These documents also comprise some general explanations on the anatomy of the human ear and the background of cochlear and vestibular sensory loss as well as the ability of known devices to restore such loss, most of this information thus not being repeated at this place for the sake of conciseness.

In particular, WO2012/012634 concerns the difficulties that face efforts to realize vestibular implants already on the level of the different kind of sensors required, namely motion sensors the position of which needs to be well determined and stable relative to the head of the patient, as compared to a relatively simple microphone used as speech sensor for cochlear implants. To optimize this aspect, WO2012/012634 proposes both internal, i.e., implanted, and external motion sensors attached to the patient's head by means of specially configured magnets.

The document U.S. Pat. No. 7,647,120 proposes a device adapted for both restoration of the auditory—and the vestibular function, since some patients suffer disorders of both of these functions. For that purpose, the proposed device comprises both a speech processor and a motion processor treating the signals from the corresponding sensors, i.e., from a microphone, respectively from the motion sensors. However, such a device necessarily is more voluminous and complicated as compared to a cochlear implant. The volume, of course, is critical for any device supposed to be, at least partially, implanted. Even more importantly, the presence of a motion processor specifically designed to treat signals from motion sensors necessitates quite important research and development and represents a potential risk on the level of the secure operation of the device as compared to the existing speech processors the performance and reliability of which are proven by years of clinical use. If fact, since vestibular implants are aimed at treatment of patients suffering from chronic disequilibrium and oscillopsia, i.e., movement of the visual field during movement of their head, malfunctioning of the implant risks to directly affect the patient's general health and security, for example because the latter could fall in case the vestibular implant fails to work correctly.

The document WO2010/135783 concerns the issue of disposing of an array of electrodes specifically adapted for implantation in a semicircular canal of the vestibular system whilst simultaneously avoiding damage to anatomical structures of the ear. For this purpose, an array of electrodes is proposed where each electrode is dimensioned and constructed such as to preserve residual vestibular function, in particular without substantially compressing the membranous labyrinth.

However, whilst the above mentioned devices and corresponding methods, like others not having been mentioned explicitly, contribute to the developments having been achieved in recent years in the field of vestibular implants, several drawbacks and problems still remain. First, electrical stimulation of neural and/or muscular tissue is required also for several other medical applications, not just for restoration of the auditory—and the vestibular function. Each of these medical applications has some specific requirements but potentially also some overlap with applications already under study since a long time, like restoration of the auditory function using cochlear implants. Such overlap could allow to use to some extent proven technology which is not fully exploited by prior art devices. Second, the development of processors specifically and almost entirely redesigned to treat signals from the specific sensors required for the given medical application represents an obstacle to rapid development as well as a potential risk for the patient, like mentioned above in the case of vestibular implants comprising a newly designed motion processor adapted to treat signals of motion sensors. Other medical applications which require a similar device adapted to be used as functional electrical stimulators are for example retinal implants, heart pacemakers, devices for functional electrical stimulation in neurological disorders such as Parkinson, etc. In most of these cases, there currently do not exist specifically adapted devices having a similar reliability and well proven functionality as compared to cochlear implants for the restoration of audition.

It is thus the object of the present invention to overcome the above mentioned difficulties and to realize a device for electrical stimulation of neural tissue adapted to be used in several medical applications. It is another objective of the present invention to extend the use of very precise, proven, and readily available medical technology like cochlear implants to a variety of related medical applications requiring electrical stimulation of neural tissue. Another objective of the present invention consists in reducing development time and cost for such devices whilst increasing the level of reliability of these devices and thus enhancing the patient's security.

To this effect, the present invention proposes a device, which is characterized by the features enumerated in the claims and which allow to achieve the objectives identified above, respectively a corresponding method according to the claims.

In particular, the device, respectively the corresponding method, according to the present invention is characterized by the fact that the device, next to comprising a known cochlear implant and at least another signal sensor, further comprises a signal transformation unit, said signal sensors being adapted to capture relevant input information and to deliver a corresponding input signal to the transformation unit, the latter allowing to transform said input signal received from the signal sensors into a modulated electrical output signal adapted to be treated by the speech processor of the cochlear implant.

More particularly, the transformation unit of such a device comprises a waveform generator adapted to generate an acoustic carrier waveform of a given frequency, at least an input allowing each for introduction of an input signal from a corresponding signal sensor connected to said input, a first amplifier allowing to amplify the signal of the acoustic carrier waveform, a third amplifier allowing to amplify the input signal, and a signal modulation component allowing to modulate in amplitude the acoustic carrier waveform generated by the waveform generator by the input signal as well as an output allowing to deliver an amplitude modulated output signal to the speech processor of the cochlear implant.

Therefore, in sum, a device, respectively a method according to the present invention allow to transform an input signal received from a large variety of signal sensors into an amplitude modulated output signal which is adapted to be treated by the speech processor of known cochlear implants, thus allowing to extend the usability of these proven devices to a variety of medical applications.

Other features and advantages of the present invention are mentioned in the dependent claims as well as in the description disclosing in the following, with reference to the figures, the invention in more detail.

BRIEF DESCRIPTION OF THE DRAWINGS

The attached figures exemplarily and schematically illustrate the principle as well as an embodiment of the present invention.

DETAILED DESCRIPTION

In the following, the invention shall be described in detail with reference to the above mentioned figures.

The present invention relates to a device, respectively a method, for electrical stimulation of neural and/or muscular tissue which in general is adapted to be used for a variety of different medical applications. A device according to the present invention comprises a cochlear implant 1 of known type being equipped at least with a power source, a speech processor 1.1.2, a current stimulator 1.2.1 and an array of electrodes 1.2.2 attached to the stimulator 1.2.1, such as schematically illustrated in FIG. 1.

Figure 1:
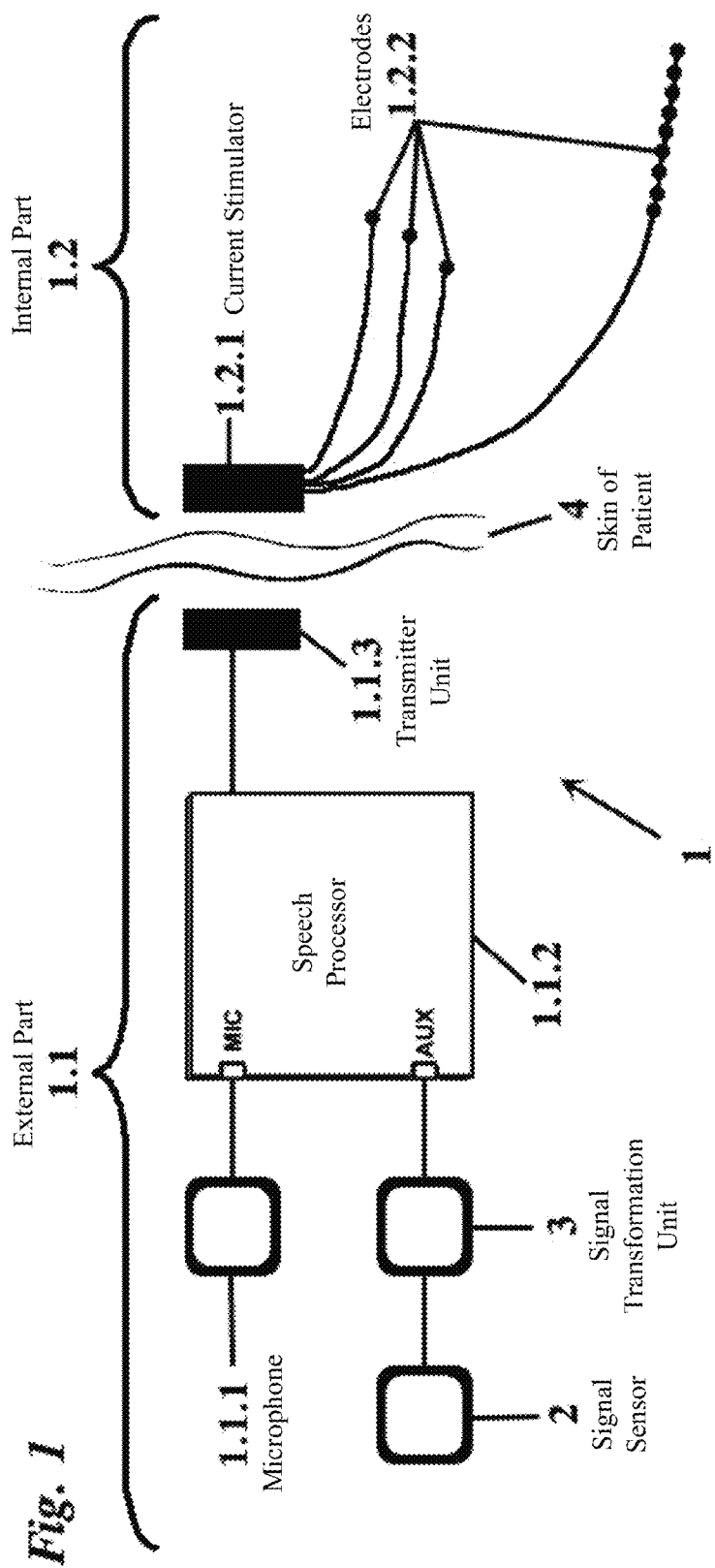
FIG. 1 schematically illustrates a device for electrical stimulation of neural and/or muscular tissue according to the present invention comprising a cochlear implant having an external part and an internal part as well as comprising a motion signal sensor and a signal transformation unit connected to the external part of the cochlear implant.

Such as depicted by way of example in FIG. 1, most cochlear implants 1 of known type comprise several components which are usually grouped in an internal part 1.2 supposed to be effectively implanted next to the patient's ear and an external part 1.1 to be worn externally, nowadays mostly in the form of a behind-the-ear-apparatus (BTE) due to the reduction in size of its electronic components. The external part 1.1 not supposed for implantation comprises a power source like a battery not shown in FIG. 1 for reasons of simplicity, a miniaturized speech processor 1.1.2, and a transmitter unit 1.1.3 connected to said processor and usually having a coil and a magnet. The role of the speech processor, sometimes also called sound processor, is to transform the output signals of a microphone 1.1.1, which is connected to the processor and by picking up sound from the environment serves as a sound sensor, into a pattern of electrical impulses adequate for activating the patient's auditory nerve. The internal part 1.2 adapted for implantation comprises a receiver unit also having a coil and a magnet, not shown in FIG. 1 for reasons of simplicity, and a current stimulator 1.2.1 with at least an array of stimulating electrodes 1.2.2 attached to it. Conventionally, the transmitter unit 1.1.3 may be fixed on the patient's head by its magnet which is placed on top of the magnet of the receiver unit of the implanted internal part 1.2. The transmitter unit 1.1.3 of the external part 1.1 and the receiver unit of the internal part 1.2 allow to transmit, by electromagnetic induction, the processed sound signals as well as the power required by the implanted components across the skin 4 of the patient. The current stimulator 1.2.1 converts the signals received from the receiver unit into electrical current impulses and sends these to at least an array of stimulating electrodes 1.2.2. For restoration of hearing loss, arrays of currently up to about two dozens of electrodes placed inside the patient's cochlea send the electrical current impulses to the auditory nerves which then transmit the information to the brain.

The development of safe and reliable components allowing to realize entirely well working cochlear implants built according to the above exposed principle was a great challenge for industry. Nevertheless, quality control and technical developments over the past 25 years now have resulted in the production of very reliable implantable stimulators.

Based on this as well as on the above mentioned fact that similar stimulators of neural tissue are also required for other medical applications, the present invention therefore proposes to extend the use of these existing reliable and sophisticated devices to other medical applications by adding supplementary means which allow to exploit cochlear implants also for other medical applications than restoration of the auditory function of a patient.

This basic idea of the present invention builds on the fact that cochlear implants are designed to transform sound signals into a pattern of electrical impulses which are adapted to be used for stimulation of neural tissue. In particular, the basic idea consists in the proposal to add to a cochlear implant supplementary means which are adapted to transform an arbitrary input signal into an electrical signal which can be fed into a speech processor of a known cochlear implant, the latter then producing signals sent to its array of electrodes which can be used to stimulate almost any given type of neural tissue.

For that purpose, the device for electrical stimulation of neural tissue according to the present invention further comprises, such as schematically illustrated in FIG. 1, at least a signal sensor 2 and a signal transformation unit 3, said signal sensors 2 being adapted to capture relevant input information and to deliver a corresponding input signal 3.2.1 to the transformation unit 3, the latter allowing to transform said input signal 3.2.1 received from the signal sensors 2 into a modulated electrical output signal 3.10.1 adapted to be treated by the speech processor 1.1.2 of the cochlear implant 1.

The above mentioned general configuration of the device for electrical stimulation of neural tissue according to the present invention shall now be described, to allow for better understanding, in the context of specific medical applications, however, without the invention being limited to these applications, since the relevant input information captured by the signal sensors 2 and transformed by the transformation unit 3 may consist in a variety of input signals depending on the given application.

An example of a medical application particularly adapted for a device as proposed is the restoration of a patient's vestibular function, especially due to the above mentioned facts that loss of the auditory—and the vestibular functions frequently occur together and that in both cases the implant should be situated close to, respectively partially in the patient's ear. Since the vestibular part of the human inner ear, the function of which is to be restored to some extent, is sensitive to motion, the signal sensors 2 in this application need to capture the motion of the patient's head. The signal sensors 2 therefore are motion sensors like gyroscopes and/or accelerometers which are known in prior art and which deliver a corresponding input signal, as such not adapted to be fed into the speech processor of a known cochlear implant, to the transformation unit 3.

Therefore, since it is desired to make use of the highly developed technology inside speech processors of known cochlear implants, it is necessary to adequately transform the motion signals coded in the output signal of the signals sensors 2 into convenient electrical signals adapted to be fed into the speech processor of the cochlear implant system. This is achieved with a small custom transformation unit 3 according to the present invention which can be attached to or form part of the components of the external part 1.1 of the cochlear implant 1. The detailed functioning of this transformation unit 3 shall now be described in the following.

However, prior to describing said transforming unit 3, it is important to review in more detail the working principles of speech processors for known cochlear implants. In brief, such speech processors are multichannel processors using the audible frequency spectrum of human speech to distribute signals across channels, respectively corresponding electrodes. All known devices are multichannel processors that divide the input sound signal into several frequency bands by using user configurable banks of bandpass filters. In each frequency band, the envelope of the signal is then extracted. This envelope signal, being usually low pass filtered, is then mapped non-linearly to current amplitude, with a compressive, often quasi-logarithmic, function. The current amplitude determined by this processing is then used, via the transmitter unit 1.1.3, the receiver unit, and the current stimulator 1.2.1 such as described above, to activate the implanted electrode attributed to this frequency band. The number of channels varies in different models and manufacturers of speech processors and is not a preliminary factor for the result obtained in terms of the quality of the speech recognition by the patient. An important factor on the result is the signal processing algorithm applied in a given speech processor, this, however, not being further discussed at this place since a transformation unit 3 according to the present invention may be used in combination with any of the currently used algorithms in known speech processors. Furthermore, it shall be pointed out at this place that the earlier speech processors were analog devices whilst nowadays digital speech processors are widely used. Also this aspect is of no importance with respect to the transformation unit 3 according to the present invention since the latter may be used in combination with any analog or digital speech processors.

Figure 2:
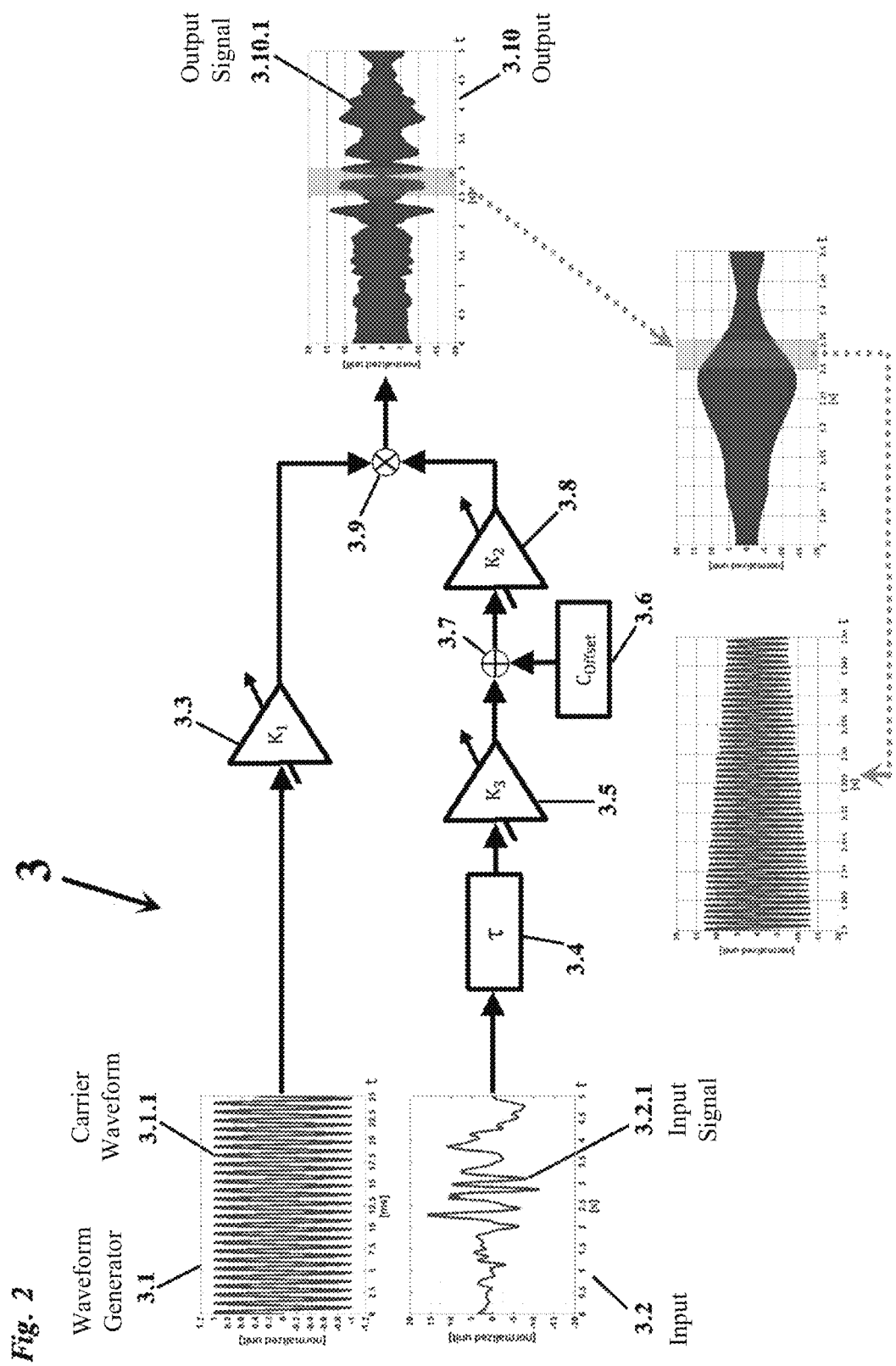
FIG. 2 schematically shows the components of the signal transformation unit according to the present invention and illustrates, by giving examples of the corresponding input and output signals of the unit, its functioning.

According to the above mentioned working principle of speech processors used in cochlear implants, the transformation unit 3 of a device according to the present invention has the following structure which is schematically illustrated in FIG. 2. The unit 3 comprises a waveform generator 3.1 which is adapted to generate an acoustic carrier waveform 3.1.1 of a given frequency. It also has at least an input 3.2 in order to allow for introduction of an input signal 3.2.1. Each input 3.2 is connected to a signal sensor 2 such that said input signal 3.2.1 corresponds to the output signal delivered by each signal sensor 2, like the gyroscopes and/or accelerometers used in the present example application of restoration of vestibular function. The transformation unit 3 furthermore comprises a first amplifier 3.3 allowing to amplify the signal of the acoustic carrier waveform 3.1.1 generated by the waveform generator 3.1. The gain created by the first amplifier 3.3 for the generated carrier acoustic waveform 3.1.1 is designated by $K_1$ in FIG. 2. The transformation unit 3 also comprises a signal delay component 3.4 and a second amplifier 3.5 allowing to amplify, by a gain $K_3$, the input signal 3.2.1 after having been delayed by component 3.4. The transformation unit 3 still comprises an offset generator 3.6 and a signal addition component 3.7 allowing to add an offset signal of a chosen height to the amplified delayed input signal 3.2.1. In order to allow to further amplify the modified input signal, the transformation unit 3 has a third amplifier 3.8 applying a gain $K_2$ to the latter signal. Finally, the transformation unit 3 comprises a signal modulation component 3.9, like a multiplier, allowing to modulate in amplitude the acoustic carrier waveform 3.1.1 generated by the waveform generator 3.1 by the—eventually offset and/or delayed—input signal 3.2.1 as well as an output 3.10 allowing to deliver an amplitude modulated output signal 3.10.1 to the speech processor 1.1.2 of the cochlear implant 1. In line with what has been explained above, the transformation unit 3 may, of course, be realized as an analog or as a digital device. By the way, any combination of an analog or digital transformation unit 3 with an analog or digital speech processor 1.1.2 is feasible.

In view of the above described structure of such a transformation unit 3, its operation mode is clear to a person skilled in the art and shall be commented shortly with the help of the following equation $$S_{Mod}(t)=K_1 S_{Carrier}(t) K_2 [C_{Offset}+K_3 S_{Sensor}(t-\tau)] \quad (I)$$

which allows to mathematically describe the function of the individual components of the transformation unit 3, where the symbols have the following meaning $S_{Mod}$=amplitude modulated signal at the output,
$S_{Sensor}$=input signals such as delivered by the signal sensors,
$S_{Carrier}$=acoustic carrier waveform,
$\tau$=time delay applied to input signals from the signal sensors,
$C_{Offset}$=constant value added to input signals from the signal sensors,
$K_1$=gain applied to carrier acoustic waveform,
$K_2$=gain applied to delayed and/or offset input signals,
$K_3$=gain applied to delayed input signals.

By using the transformation unit 3, an input signal 3.2.1 delivered by any given signal sensor 2 and called $S_{Sensor}$ in equation I, thus can be delayed by a time interval $\tau$ and then amplified by gain $K_3$, the resulting signal then being, if necessary, offset by a constant value $C_{Offset}$ and again amplified by gain $K_2$. The thus obtained signal serves to modulate in amplitude the carrier acoustic waveform 3.1.1, called $S_{Carrier}$ in equation I, after amplification of the latter by gain $K_1$, the resulting amplitude modulated signal 3.10.1, called $S_{Mod}$ in equation I, being delivered to the output 3.10 of unit 3. It is a mandatory prerequisite that the frequency of the acoustic carrier waveform 3.1.1, e.g., 1000 Hz, is chosen to be situated in a given frequency band, i.e., a given channel, of the speech processor 1.1.2 of the cochlear implant 1, in other words that it lies inside the operating frequency range of the speech processors (usually 0 Hz-8000 Hz), in order to allow that the amplitude modulated signal 3.10.1 is adapted to be fed into any speech processor 1.1.2 of known cochlear implants which then will deliver adequate electrical current signals to stimulate neural and/or muscular tissue.

The use of a transformation unit 3 as well as the detailed function of its components, respectively the use of a device for stimulation of neural and/or muscular tissue according to the present invention shall now be described in more detail by reverting back to the above mentioned example application of restoration of the vestibular function. The case of unilateral implantation of such a device shall be discussed first, since this configuration is different from bilateral implantation, as will become clear in the following.

In fact, clinical experiments conducted by the applicant have shown that by use of a transformation unit 3 in connection with a unilateral cochlear implant 1, smooth eye movements can be elicited by unilateral stimulation of one branch of the vestibular nerve using amplitude modulated trains of bi-phasic pulses, i.e., pulses comprising both positive and negative phases. However, in case of only unilateral stimulation of the vestibular system, one prerequisite before any attempt to drive smooth eye movements in both directions of a given spatial dimension is to re-establish a non-zero artificial neural baseline activity such that it can be up or down modulated by electrical stimulation, such activity mimicking spontaneous rate firing in the normal nerve (Guyot et al. 2011, *Annals of Otology, Rhinology & Laryngology* 120(2):81-87; Guyot et al. 2011, *Annals of Otology, Rhinology & Laryngology* 120(3):143-149). Briefly, this is due to the fact that in a normally functioning vestibular system, motion is coded by modulation of the spontaneous firing rate of the vestibular nerves. For example, for the horizontal semicircular canal of each ear, a head rotation in the direction of the canal, i.e., rightwards for the right ear and leftwards for the left ear, will result in an increase of the firing rate, which will in turn result in a compensatory horizontal eye movement in the opposite direction, i.e., leftwards for the right ear and rightwards for the left ear. Conversely, a horizontal head rotation in the reverse direction will result in a decrease of the firing rate and accordingly in a compensatory horizontal eye movement in the other direction. However, in patients with bilateral vestibular areflexia, a neural baseline activity does not exist. Therefore, a prerequisite to reestablish bi-directional eye movements with a unilateral implant is to restore an artificial baseline activity so that it can be increased (up-modulated) for generating eye movements in one direction and decreased (down-modulated) for generating eye movements in the opposite direction. Re-establishment of the desired artificial neural baseline activity is achieved by allowing the patient to adapt to an unmodulated, i.e., constant amplitude, train of bi-phasic pulses until any residual nystagmic responses and vestibular symptoms vanish, which usually takes a few minutes, this being possible due to the natural adaptation capacity of the human vestibular system.

Therefore, in order to realize this adaptation phase, the transformation unit 3 needs to be able to produce an adequate stimulus that will result in a constant amplitude bi-phasic pulse train at the output of the current stimulator 1.2.1 of the cochlear implant 1. Given the above described structure and operation mode of the transformation unit 3, this can be achieved by setting the gain $K_3$ applied to the input signal $S_{Sensor}$ to 0, which corresponds to no motion, and adjusting the constant value $C_{Offset}$ such that $C_{Offset} * K_2=1$. In that case, equation I simplifies to $S_{Mod}(t)=K_1 S_{Carrier}(t)$. The gain $K_1$ can now be adjusted to result in a given constant stimulation amplitude at the output of the current stimulator 1.2.1 of the cochlear implant 1. Said constant stimulation amplitude depends on the patient's dynamic range and on the particular cochlear stimulator transfer function.

After completion of the adaptation phase, recognizable by the patient in that any residual nystagmic response and vestibular symptoms like vertigo and dizziness vanish, motion modulated stimulation can be initiated by setting the gain $K_3$ applied to the input signal $S_{Sensor}$ to 1, thus effectively re-feeding signals delivered by the motion sensor 2 into the transformation unit 3. The final fine tuning of the transformation unit 3 is achieved by re-adjusting parameters $K_1$, $\tau$, $C_{Offset}$, and $K_2$ according to the patient's sensitivity and dynamic range, i.e., his vestibular perception threshold, and to the characteristics of the motion sensors 2 selected, e.g., by applying a steady-state offset and gain, in order to achieve a given range of stimulation current patterns in response to a given range of head motion patterns. Whilst the function and advantage of the other parameters has become clear from the above, it should still be noted at this place that, as far as is concerned the delay time $\tau$, in all sensory systems there is a certain delay between the actual physical stimulus, like light, sound, motion, etc., and the physiological response. This delay varies from one sensory system to the other and, in the case of the vestibular system, has been estimated to be of about 10 ms. When considering artificial systems intending to restore a given function via electrical stimulation, the delay between the stimulus and the stimulation is practically null, since all peripheral processing of the sensory apparatus is bypassed. Therefore, depending on the system, it might be necessary to introduce a delay time $\tau$ between the stimulus detected by the sensor and the electrical stimulation sent to the target nerve. Therefore, this delay may be taken into consideration in the transformation unit 3 by applying a delay time $\tau$ to the input signal 3.2.1 delivered by the signal sensors 2. In sum, it can be easily seen from the above described example that the parameters $K_1$, $\tau$, $C_{Offset}$, and $K_2$ of equation I can be readily adjusted and should be determined according to the particular requirements of the given medical application.

Furthermore, by using the above described coding strategy for the transformation unit 3 and in order to allow in the example of the vestibular system coding movements in all different spatial dimensions, multichannel stimulation can be easily achieved by using different frequencies for the corresponding acoustic carrier waveforms 3.1.1, e.g., 1000 Hz, 2000 Hz and 3000 Hz, the only requirement being that these frequencies are inside the operating range of the sound processor (typically 0 Hz-8000 Hz) and are configured to belong to different channels of the multichannel speech processor 1.1.2 in use. For example, for stimulating three electrodes 1.2.2 corresponding to the three nerve branches of the vestibular system in each ear, three frequency bands have to be selected, i.e., one for each channel, respectively each electrode. Otherwise, the procedure described above for the transformation unit 3 can be replicated entirely for each individual channel, with the only differences being that the acoustic carrier waveform 3.1.1 of each channel has a different frequency, corresponding to the frequency bands chosen, and that the signals coming from each channel have to be merged together, e.g., by addition, to form the output signal 3.10.1 of the transformation unit 3. Correspondingly, insofar the frequencies for the corresponding acoustic carrier waveforms 3.1.1 of the individual channels have not been chosen in advance according to the frequency bands of the speech processor 1.1.2 of the cochlear implant 1 in use, the latter will have to be configured appropriately so that stimulation signals originated by each channel are distributed coherently along the corresponding vestibular electrodes.

To come now to the case of bilateral implantation of a device according to the present invention, it should be noted, as already mentioned before, that for restoration of the vestibular function with a unilateral vestibular neuroprosthesis, an artificial neural baseline activity has to be re-established such that it can be up or down modulated by electrical stimulation. In the case of bilateral vestibular implants, i.e., implantation of one device in each ear, this is not necessary, for the reasons figuring above, given that up-modulation in one ear will generate eye movements in one direction and up-modulation in the other ear will result in eye movements in the opposite direction. In this case, the transformation unit 3 thus can be directly set up to generate a given range of stimulation current patterns in response to a given range of head motion patterns without requiring prior re-establishment of any baseline, steady-state stimulation. Therefore, the above mentioned adaptation phase of the patient is not required in this case and a "no motion" or "zero motion" output of the signal sensors 2 will result in zero current stimulation of the neural tissue. Therefore, the parameters $K_1$, $\tau$, $C_{Offset}$, and $K_2$ in equation I should in the case of bilateral vestibular implants be adjusted such that the resulting modulated stimulation currents vary between zero and the upper comfortable level of stimulation for a given patient.

Moreover, the person skilled in the art will have noted that the proposed device is particularly advantageous for simultaneous restoration of the cochlear—and the vestibular functions. In that case, two types of signal sensors 2 are required, namely a microphone 1.1.1 for capture of environmental sound and at least a motion sensor 2. Due to the fact that almost all known cochlear implants 1, respectively their speech processors 1.1.2 have an AUX input, the modulated signal 3.10.1 delivered by the transformation unit 3 can, like in the configurations describe above, easily be fed into the speech processor 1.1.2, next to the sound signal delivered by the microphone 1.1.1 into the MIC input of the speech processor 1.1.2, such as schematically shown in FIG. 1. The two signals from the microphone 1.1.1 and from the transformation unit 3 are merged together at the input of the speech processor 1.1.2. This usually is done automatically by the speech processor 1.1.2, but could also be done in the transformation unit 3 if the processor cannot use both the microphone 1.1.1 and auxiliary input simultaneously. Then, the frequency bands of the processor 1.1.2 have to be configured appropriately, which is possible since user configurable, such that stimulation signals coming from sound stimuli are distributed on cochlear electrodes, and stimulation signals coming from motion stimuli are distributed on vestibular electrodes. Note that in this particular case, the frequency bands chosen for the transformation unit 3 processing vestibular stimuli preferentially are situated outside of the range of frequencies required for human speech, i.e., outside the range of 100 Hz to 8000 Hz, if the cochlear implant 1 in use allows to treat frequencies slightly below 100 Hz or slightly above 8000 Hz. Otherwise, given that it is not necessary to use all cochlear electrodes for obtaining good speech recognition results, it is alternatively also possible to use in this specific case of simultaneous restoration of the cochlear—and the vestibular functions three channels for the vestibular electrodes situated inside the range of 100 Hz to 8000 Hz, these channels thus not being connected to cochlear electrodes.

Anyway, the at least one array of electrodes 1.2.2 attached to the implanted stimulator 1.2.1 of the cochlear implant in use needs to be adapted to the anatomy of the neural target, e.g., in the above example application to the anatomy of the branches of the vestibular nerve. As mentioned in the introduction, adequate electrode arrays are known in prior art and these can easily be connected to a given cochlear implant 1. Also, cochlear implant manufacturers in general have extensive experience in producing different types of implantable electrodes for vestibular as well as other neural targets, such that this part of the cochlear implant 1 may conveniently be exchanged depending on or adapted to the medical application, respectively the target neural and/or muscular tissue.

The same applies, of course, to the signal sensors 2 which need to be adapted to the medical application for which the device according to the present invention should be used. Again, a number of adequate signal sensors 2, which as such are not subject of the present invention, can be found in prior art and connected to the transformation unit 3, like for example known motion sensors in case of restoration of the vestibular function.

Finally, recent efforts have been directed to realize cochlear implants the components of which are not separated into an external—and an internal part, but are designed to be fully implanted. In these devices, the transmitter and receiver units such as mentioned in the context of the above described currently used cochlear implants are used only for a subset of functions like programming the stimulator and recharging the batteries when required, respectively may be completely omitted. It is, however, clear that if such fully implantable cochlear implants, currently still in the development phase, will become available in future, they could be used in the context of a device for stimulation of neural or muscular tissue according to the present invention, the latter thus comprising, in a minimal configuration, a fully or partially implantable cochlear implant 1 being equipped with a power source, a speech processor 1.1.2, a current stimulator 1.2.1 and at least an array of electrodes 1.2.2 attached to the stimulator 1.2.1, at least a signal sensor 2, and a transformation unit 3.

Moreover, the present invention is also related to a corresponding method for electrical stimulation of neural and/or muscular tissue. In particular, a corresponding method for electrical stimulation of neural and/or muscular tissue comprises the steps of:

providing a cochlear implant 1 being equipped with a power source, a speech processor 1.1.2, a current stimulator 1.2.1 and at least an array of electrodes 1.2.2 attached to the stimulator 1.2.1, providing at least a signal sensor 2, and providing a signal transformation unit 3, said signal sensors 2 being adapted to capture relevant input information and to deliver a corresponding input signal 3.2.1 to the transformation unit 3, the latter allowing to transform said input signal 3.2.1 received from the signal sensors 2 into a modulated electrical output signal 3.10.1 adapted to be treated by the speech processor 1.1.2 of the cochlear implant 1.

Such a method more particularly includes the steps of:

generating an acoustic carrier waveform 3.1.1 of a given frequency by a waveform generator 3.1 of the transformation unit 3, introducing at least an input signal 3.2.1 from a corresponding signal sensor 2 into at least an input 3.2 of the transformation unit 3, amplifying the signal of the acoustic carrier waveform 3.1.1 by a first amplifier 3.3 of the transformation unit 3, if desired, applying a delay interval $\tau$ to the input signal 3.2.1 by a signal delay component 3.4 of the transformation unit 3 and amplifying the delayed signal by a second amplifier 3.5 and/or adding an offset signal of a chosen height $C_{Offset}$ to the input signal 3.2.1 by an offset generator 3.6 as well as a signal addition component 3.7 of the transformation unit 3, amplifying the resulting input signal 3.2.1 by a third amplifier 3.8 of the transformation unit 3, and modulating in amplitude the acoustic carrier waveform 3.1.1 generated by the waveform generator 3.1 by the resulting input signal 3.2.1 by a signal modulation component 3.9 of the transformation unit 3, as well as delivering an amplitude modulated output signal 3.10.1 to the speech processor 1.1.2 of the cochlear implant 1 by an output 3.10 of the transformation unit 3.

Therefore, the transformation of said input signal 3.2.1 received from the signal sensors 2 into a modulated electrical output signal 3.10.1 applied by the transformation unit 3 is described by equation:

$$S_{Mod}(t) = K_1 S_{Carrier}(t) K_2 [C_{Offset} + K_3 S_{Sensor}(t-\tau)],$$

$S_{Mod}$ being the amplitude modulated signal at the output, $S_{Sensor}$ being the input signals delivered by the signal sensors, $S_{Carrier}$ being the acoustic carrier waveform, $\tau$ being the time delay applied to the input signals, $C_{Offset}$ being the constant value added to input signals, $K_1$ being the gain applied to carrier acoustic waveform, $K_2$ being the gain applied to delayed and/or offset input signals, $K_3$ being the gain applied to delayed input signals.

This procedure allows to map an almost arbitrary input signal into a given pattern of electrical output signals adapted to be used by the speech processor of a cochlear implant, thus to use the latter as universal electrical stimulators.

In the particular application of vestibular implants with unilateral implantation of the cochlear implant 1, the method also comprises performing an adaptation phase which comprises the steps of:

setting the gain $K_3$ applied to the input signal $S_{Sensor}$ to 0, adjusting the constant value $C_{Offset}$ such that $C_{Offset} * K_2 = 1$, adjusting the gain $K_1$ to result in a given constant stimulation amplitude at the output of the current stimulator 1.2.1 of the cochlear implant 1, said constant stimulation amplitude depending on a given patient's dynamic range and on the transfer function of the current stimulator 1.2.1 of a given cochlear implant 1, this allowing to re-establish a non-zero artificial neural baseline activity such that it can be up or down modulated by electrical stimulation, such activity mimicking spontaneous rate firing in a normal nerve to be stimulated.

In both cases of unilateral or bilateral implantation of the cochlear implant 1, the method comprises performing an initialization phase of a sensor driven modulated stimulation by:

setting the gain $K_3$ applied to the input signal $S_{Sensor}$ to 1, thus effectively re-feeding signals delivered by the motion sensors 2 into the transformation unit 3, fine tuning of the transformation unit 3 by re-adjusting the parameters $K_1$, $\tau$, $C_{Offset}$, and $K_2$ according to a given patient's sensitivity and dynamic range concerning the neural tissue to be stimulated, and according to the characteristics of the motion sensors 2, this allowing to achieve a given range of stimulation current patterns in response to a given range of signal patterns delivered by the signal sensors 2 to the transformation unit 3.

In light of the above description of the structure and of the operating mode of a device according to the present invention, respectively of the steps of a corresponding method, its advantages are clear. Primarily, this allows to realize a device for electrical stimulation of neural and/or muscular tissue adapted to be used in several medical applications. By this means, it is possible to extend the use of very precise, proven, and readily available medical technology like cochlear implants to a variety of related medical applications requiring electrical stimulation of neural and/or muscular tissue. The device is particularly adapted for restoration of the vestibular function, especially in combination with restoration of the auditory function. At the same time, the development time and cost for such devices are considerably reduced whilst the level of reliability of these devices is increased. Altogether, this allows to propose more rapidly and at lower cost advanced treatment means to patients suffering of a variety of disfunctions whilst simultaneously enhancing the patient's security.

The invention claimed is:

1. A device for electrical stimulation of neural and/or muscular tissue, the device comprising a cochlear implant being equipped with a power source, a speech processor, a microphone adapted to deliver sound signals to said speech processor, a current stimulator, at least an array of electrodes attached to the stimulator, and at least a signal sensor other than said microphone, and a signal transformation unit;

wherein said signal sensors are adapted to capture relevant input information and to deliver a corresponding input signal to the transformation unit, the latter allowing to transform said input signal received from the signal sensors into a modulated electrical output signal adapted to be treated by the speech processor of the cochlear implant; and wherein the transformation unit comprises a waveform generator adapted to generate an acoustic carrier waveform of a given frequency, at least an input allowing for introduction of an input signal from a corresponding signal sensor connected to said input, a first amplifier allowing to amplify the signal of the acoustic carrier waveform, a third amplifier allowing to amplify the input signal, and a signal modulation component allowing to modulate in amplitude the acoustic carrier waveform generated by the waveform generator by the input signal as well as an output allowing to deliver an amplitude modulated output signal to the speech processor of the cochlear implant; and wherein the transformation unit further comprises a signal delay component and a second amplifier allowing to amplify the input signal after application of a delay interval by the signal delay component and/or an offset generator as well as a signal addition component allowing to add an offset signal of a chosen height to the input signal, such that said input signal may be delayed and/or offset before being amplified by the third amplifier and used by the signal modulation component to modulate in amplitude the acoustic carrier waveform to produce the amplitude modulated output signal of the transformation unit.

2. The device according to claim 1, wherein the transformation of said input signal received from the signal sensors into a modulated electrical output signal applied by the transformation unit is described by equation $$S_{Mod}(t)=K_1 S_{Carrier}(t) K_2 [C_{Offset}+K_3 S_{Sensor}(t-\tau)],$$

$S_{Mod}$ being the amplitude modulated signal at the output,
$S_{Sensor}$ being the input signals delivered by the signal sensors,
$S_{Carrier}$ being the acoustic carrier waveform,
$\tau$ being the time delay applied to the input signals,
$C_{Offset}$ being the constant value added to input signals,
$K_1$ being the gain applied to carrier acoustic waveform,
$K_2$ being the gain applied to delayed and/or offset input signals,
$K_3$ being the gain applied to delayed input signals.

3. The device according to claim 1, wherein a frequency of the acoustic carrier waveform is chosen such as to be situated in a given frequency band, respectively a given channel, of the speech processor of the cochlear implant.

4. The device according to claim 3, wherein the frequency of the acoustic carrier waveform lies inside the frequency range suitable to be processed by the speech processor of the cochlear implant, in particular lies in the frequency range 0 Hz-8000 Hz.

5. The device according to claim 1, wherein the transformation unit is realized as an analog or as a digital device.

6. The device according to claim 1, wherein the signal sensor is adapted to capture relevant input information.

7. The device according to claim 6, wherein the relevant input information includes motion information.

8. The device according to claim 1, wherein the signal sensor is chosen from the group comprising a gyroscope, and an accelerometer.

9. The device according to claim 1, comprising signal sensors of different type adapted to capture relevant input information for different medical applications, in particular that it comprises a gyroscope, and/or an accelerometer, thus allowing the device to be used for restoration of the auditory and the vestibular function of a patient.

10. The device according to claim 1, wherein the cochlear implant is adapted for partial implantation and has an external part not supposed for implantation comprising said power source, said speech processor and a transmitter unit connected to said processor as well as an internal part adapted for implantation comprising a receiver unit, said current stimulator and said array of electrodes attached to the stimulator.

11. The device according to claim 1, wherein the cochlear implant is adapted for full implantation and only has an internal part adapted for implantation comprising said power source, said speech processor, said current stimulator and said array of electrodes attached to the stimulator.

12. A method for electrical stimulation of neural and/or muscular tissue, the method comprising the steps of:

providing a cochlear implant being equipped with a power source, a speech processor, a current stimulator and at least an array of electrodes attached to the stimulator,
providing at least a signal sensor,
providing a signal transformation unit,
said signal sensors being adapted to capture relevant input information and to deliver a corresponding input signal to the transformation unit,
the transformation unit allowing to transform said input signal received from the signal sensors into a modulated electrical output signal adapted to be treated by the speech processor of the cochlear implant,
generating an acoustic carrier waveform of a given frequency by a waveform generator of the transformation unit,
introducing at least an input signal from a corresponding signal sensor into at least an input of the transformation unit,
amplifying the signal of the acoustic carrier waveform by a first amplifier of the transformation unit,
applying a delay interval to the input signal by a signal delay component of the transformation unit and amplifying the delayed signal by a second amplifier and/or adding an offset signal of a chosen height to the input signal by an offset generator as well as a signal addition component of the transformation unit,
amplifying the resulting input signal by a third amplifier of the transformation unit, and
modulating in amplitude the acoustic carrier waveform generated by the waveform generator by the resulting input signal by a signal modulation component of the transformation unit, and
delivering an amplitude modulated output signal to the speech processor of the cochlear implant by an output of the transformation unit,
such that the transformation of said input signal received from the signal sensors into a modulated electrical output signal applied by the transformation unit is described by equation:

$$S_{Mod}(t)=K_1 S_{Carrier}(t) K_2 [C_{Offset}+K_3 S_{Sensor}(t-\tau)],$$

$S_{Mod}$ being the amplitude modulated signal at the output, $S_{Sensor}$ being the input signals delivered by the signal sensors, $S_{Carrier}$ being the acoustic carrier waveform, $\tau$ being the time delay applied to the input signals, $C_{Offset}$ being the constant value added to input signals, $K_1$ being the gain applied to carrier acoustic waveform, $K_2$ being the gain applied to delayed and/or offset input signals, $K_3$ being the gain applied to delayed input signals.

13. The method according to claim 12, wherein the method further comprises, in case of unilateral implantation of the cochlear implant for vestibular stimulation, performing an adaptation phase which comprises the steps of setting the gain ($K_3$) applied to the input signal $S_{Sensor}$ to 0, adjusting the constant value $C_{Offset}$ such that $C_{Offset}*K_2=1$, adjusting the gain $K_1$ to result in a given constant stimulation amplitude at the output of the current stimulator of the cochlear implant, said constant stimulation amplitude depending on a given patient's dynamic range and on the transfer function of the current stimulator of a given cochlear implant, this allowing to re-establish a non-zero artificial neural baseline activity such that it can be up or down modulated by electrical stimulation, such activity mimicking spontaneous rate firing in a normal nerve to be stimulated, and, in both cases of unilateral or bilateral implantation of the cochlear implant for vestibular stimulation, performing an initialization phase of a sensor driven modulated stimulation by setting the gain ($K_3$) applied to the input signal $S_{Sensor}$ to 1, thus effectively (re-)feeding signals delivered by the motion sensors into the transformation unit, fine tuning of the transformation unit by re-adjusting the parameters $K_1$, $\tau$, $C_{Offset}$, and $K_2$ according to a given patient's sensitivity and dynamic range concerning the neural tissue to be stimulated, and according to the characteristics of the motion sensors, in order to achieve a given range of stimulation current patterns in response to a given range of signal patterns delivered by the signal sensors to the transformation unit.

14. A device for electrical stimulation of neural and/or muscular tissue, the device comprising a cochlear implant being equipped with a power source, a speech processor, a microphone adapted to deliver sound signals to said speech processor, a current stimulator, at least an array of electrodes attached to the stimulator, and at least a signal sensor other than said microphone, and a signal transformation unit;

wherein said signal sensors are adapted to capture relevant input information and to deliver a corresponding input signal to the transformation unit, the latter allowing to transform said input signal received from the signal sensors into a modulated electrical output signal adapted to be treated by the speech processor of the cochlear implant; and wherein the transformation of said input signal received from the signal sensors into a modulated electrical output signal applied by the transformation unit is described by equation $$S_{Mod}(t)=K_1 S_{Carrier}(t) K_2 [C_{Offset}+K_3 S_{Sensor}(t-\tau)],$$

$S_{Mod}$ being the amplitude modulated signal at the output, $S_{Sensor}$ being the input signals delivered by the signal sensors, $S_{Carrier}$ being the acoustic carrier waveform, $\tau$ being the time delay applied to the input signals, $C_{Offset}$ being the constant value added to input signals, $K_1$ being the gain applied to carrier acoustic waveform, $K_2$ being the gain applied to delayed and/or offset input signals, $K_3$ being the gain applied to delayed input signals.

15. The device according to claim 14, wherein the transformation unit comprises a waveform generator adapted to generate an acoustic carrier waveform of a given frequency, at least an input allowing for introduction of an input signal from a corresponding signal sensor connected to said input, a first amplifier allowing to amplify the signal of the acoustic carrier waveform, a third amplifier allowing to amplify the input signal, and a signal modulation component allowing to modulate in amplitude the acoustic carrier waveform generated by the waveform generator by the input signal as well as an output allowing to deliver an amplitude modulated output signal to the speech processor of the cochlear implant.

16. The device according to claim 15, wherein the transformation unit further comprises a signal delay component and a second amplifier allowing to amplify the input signal after application of a delay interval by the signal delay component and/or an offset generator as well as a signal addition component allowing to add an offset signal of a chosen height to the input signal, such that said input signal may be delayed and/or offset before being amplified by the third amplifier and used by the signal modulation component to modulate in amplitude the acoustic carrier waveform to produce the amplitude modulated output signal of the transformation unit.

17. The device according to claim 14, wherein a frequency of the acoustic carrier waveform is chosen such as to be situated in a given frequency band, respectively a given channel, of the speech processor of the cochlear implant.

18. The device according to claim 17, wherein the frequency of the acoustic carrier waveform lies inside the frequency range suitable to be processed by the speech processor of the cochlear implant, in particular lies in the frequency range 0 Hz-8000 Hz.

19. The device according to claim 14, wherein the transformation unit is realized as an analog or as a digital device.

20. The device according to claim 14, wherein the signal sensor is adapted to capture relevant input information.

21. The device according to claim 20, wherein the relevant input information includes motion information.

22. The device according to claim 14, wherein the signal sensor is chosen from the group comprising a gyroscope, and an accelerometer.

23. The device according to claim 14, comprising signal sensors of different type adapted to capture relevant input information for different medical applications, in particular that it comprises a gyroscope, and/or an accelerometer, thus allowing the device to be used for restoration of the auditory and the vestibular function of a patient.

24. The device according to claim 14, wherein the cochlear implant is adapted for partial implantation and has an external part not supposed for implantation comprising said power source, said speech processor and a transmitter unit connected to said processor as well as an internal part adapted for implantation comprising a receiver unit, said current stimulator and said array of electrodes attached to the stimulator.

25. The device according to claim 14, wherein the cochlear implant is adapted for full implantation and only has an internal part adapted for implantation comprising said power source, said speech processor, said current stimulator and said array of electrodes attached to the stimulator.

26. A method for electrical stimulation of neural and/or muscular tissue, the method comprising the steps of:

providing a cochlear implant being equipped with a power source, a speech processor, a current stimulator and at least an array of electrodes attached to the stimulator, providing at least a signal sensor, and providing a signal transformation unit, said signal sensors being adapted to capture relevant input information and to deliver a corresponding input signal to the transformation unit, the transportation unit allowing to transform said input signal received from the signal sensors into a modulated electrical output signal adapted to be treated by the speech processor of the cochlear implant wherein the method further comprises, in case of unilateral implantation of the cochlear implant for vestibular stimulation, performing an adaptation phase which comprises the steps of setting the gain ($K_3$) applied to the input signal $S_{Sensor}$ to 0, adjusting the constant value $C_{Offset}$ such that $C_{Offset}*K_2=1$, adjusting the gain $K_1$ to result in a given constant stimulation amplitude at the output of the current stimulator of the cochlear implant, said constant stimulation amplitude depending on a given patient's dynamic range and on the transfer function of the current stimulator of a given cochlear implant, this allowing to re-establish a non-zero artificial neural baseline activity such that it can be up or down modulated by electrical stimulation, such activity mimicking spontaneous rate firing in a normal nerve to be stimulated, and, in both cases of unilateral or bilateral implantation of the cochlear implant for vestibular stimulation, performing an initialization phase of a sensor driven modulated stimulation by setting the gain ($K_3$) applied to the input signal $S_{Sensor}$ to 1, thus effectively (re-)feeding signals delivered by the motion sensors into the transformation unit, fine tuning of the transformation unit by re-adjusting the parameters $K_1$, $\tau$, $C_{Offset}$, and $K_2$ according to a given patient's sensitivity and dynamic range concerning the neural tissue to be stimulated, and according to the characteristics of the motion sensors, in order to achieve a given range of stimulation current patterns in response to a given range of signal patterns delivered by the signal sensors to the transformation unit.

27. The method according to claim 26, further comprising the steps of:

generating an acoustic carrier waveform of a given frequency by a waveform generator of the transformation unit, introducing at least an input signal from a corresponding signal sensor into at least an input of the transformation unit, amplifying the signal of the acoustic carrier waveform by a first amplifier of the transformation unit, applying a delay interval to the input signal by a signal delay component of the transformation unit and amplifying the delayed signal by a second amplifier and/or adding an offset signal of a chosen height to the input signal by an offset generator as well as a signal addition component of the transformation unit, amplifying the resulting input signal by a third amplifier of the transformation unit, and modulating in amplitude the acoustic carrier waveform generated by the waveform generator by the resulting input signal by a signal modulation component of the transformation unit, and delivering an amplitude modulated output signal to the speech processor of the cochlear implant by an output of the transformation unit, such that the transformation of said input signal received from the signal sensors into a modulated electrical output signal applied by the transformation unit is described by equation:

$$S_{Mod}(t)=K_1 S_{Carrier}(t) K_2 [C_{Offset}+K_3 S_{Sensor}(t-\tau)],$$

$S_{Mod}$ being the amplitude modulated signal at the output, $S_{Sensor}$ being the input signals delivered by the signal sensors, $S_{Carrier}$ being the acoustic carrier waveform, $\tau$ being the time delay applied to the input signals, $C_{Offset}$ being the constant value added to input signals, $K_1$ being the gain applied to carrier acoustic waveform, $K_2$ being the gain applied to delayed and/or offset input signals, $K_3$ being the gain applied to delayed input signals.

* * * * *